(12) United States Patent
Nelson

(10) Patent No.: US 7,909,841 B1
(45) Date of Patent: Mar. 22, 2011

(54) CO-AXIAL ACTUATED SCISSORS

(76) Inventor: Chris L. Nelson, North East, PA (US)

( * ) Notice: Subject to any disclaimer, the term of this patent is extended or adjusted under 35 U.S.C. 154(b) by 940 days.

(21) Appl. No.: 11/536,053

(22) Filed: Sep. 28, 2006

(51) Int. Cl.
*A61B 17/32* (2006.01)
(52) U.S. Cl. .......................... 606/174; 30/194
(58) Field of Classification Search .......... 606/174, 606/167, 170, 110, 205, 120, 145, 206, 207, 606/208; 30/194, 196, 199, 205, 235; 132/73, 132/75.4, 75.5
See application file for complete search history.

(56) References Cited

U.S. PATENT DOCUMENTS

| | | | |
|---|---|---|---|
| 139,983 | A | 6/1873 | Van Hoosen |
| 321,721 | A | 7/1885 | Haasan |
| 422,670 | A | 3/1890 | Wallace |
| 483,550 | A | 10/1892 | Gerard |
| 801,471 | A | 10/1905 | Miller |
| 858,003 | A | 6/1907 | Klever |
| 966,269 | A | 8/1910 | Underwood |
| D057,749 | S | 4/1921 | Wackt |
| 1,663,761 | A * | 3/1928 | Johnson .................. 606/159 |
| 1,904,399 | A | 4/1933 | Balthaser |
| D198,963 | S | 8/1964 | Ericson |
| D310,714 | S | 9/1990 | Dolwick |
| 5,536,251 | A * | 7/1996 | Evard et al. .............. 604/93.01 |
| 5,603,723 | A * | 2/1997 | Aranyi et al. .............. 606/205 |
| 5,618,305 | A | 4/1997 | Lolagne |
| 5,643,303 | A * | 7/1997 | Donahue .................. 606/170 |
| 5,746,748 | A | 5/1998 | Steinberg et al. |
| 5,746,757 | A | 5/1998 | McGuire |
| 5,800,449 | A | 9/1998 | Wales |
| 5,891,161 | A | 4/1999 | Graser |
| 5,997,565 | A | 12/1999 | Inoue |
| 6,001,116 | A | 12/1999 | Heisler et al. |
| 6,513,247 | B1 | 2/2003 | Krasik-Geiger et al. |

FOREIGN PATENT DOCUMENTS

GB 2069912 A 9/1983
RU 1814541 5/1993

\* cited by examiner

*Primary Examiner* — Anhtuan T Nguyen
*Assistant Examiner* — Jonathan W Miles
(74) *Attorney, Agent, or Firm* — Wayne L. Lovercheck

(57) ABSTRACT

Co-axial actuated scissors for slidable positioning along a nerve for cutting the nerve or other anatomical surgical structure in a plane normal to the longitudinal axis of the scissors and away from the surgery site without harming adjacent tissues includes a first scissor portion having an offset handle attached to a slotted cylinder and a second scissor portion having an offset handle attached to an inner cylindrical member with the inner member telescoped within the slotted cylinder for concentric rotation therewith and the slotted cylinder and rotating member defining the longitudinal axis such that the cylinder and the rotating member include a loop end comprising a pair of cutting jaws whose cutting action is normal to the longitudinal axis and which are movable from an open position to a gripping position to a fully closed position for cutting the nerve through rotatable concentric actuation of the rotating member relative to the slotted cylinder and with detents positioned on an arcuate arm of the first scissor portion successively engaging a receiving notch located on the handle of the second scissor portion for holding the cutting jaws in each position as needed in order to effectuate the surgical operation.

13 Claims, 14 Drawing Sheets

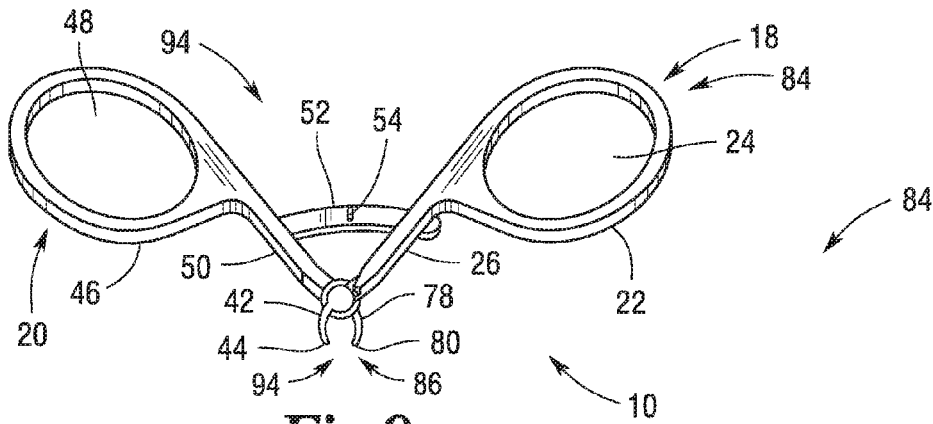
Fig. 9
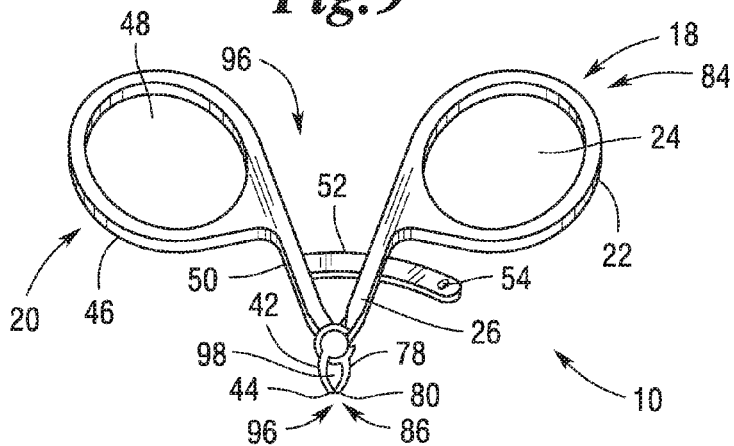
Fig. 10
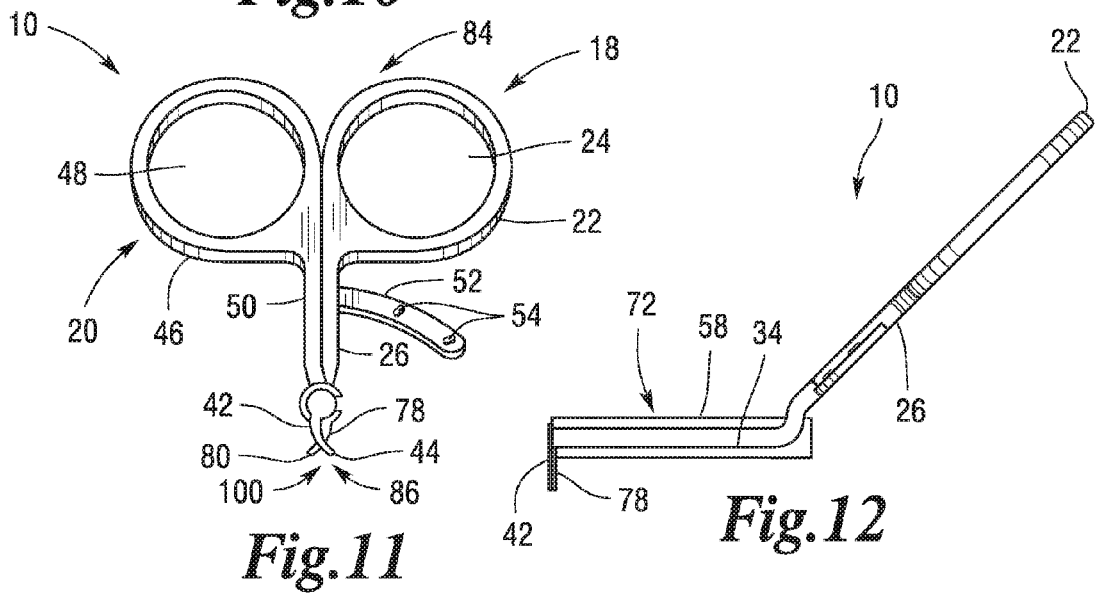
Fig. 11
Fig. 12

CO-AXIAL ACTUATED SCISSORS

FIELD OF THE INVENTION

The present invention pertains to surgical cutting instruments, and more particularly pertains to surgical scissors having cutting blades that cut at an orientation normal to the primary axis through which the handles travel for the co-axial actuation of the cutting blades.

BACKGROUND OF THE INVENTION

In cutting or severing a nerve or other anatomical structure a number of critical factors and circumstances must be taken into consideration for achievement of a successful surgical procedure. The actual cutting action, for example, must be accomplished without cutting any adjacent structure, and such cutting action often doesn't require direct visualization of the structure being cut. Indeed, with certain types of surgical procedures, non-visualization is often preferred. Moreover, there are other procedures, such as common digital neuroma excision in the foot, where severance of the nerve as far away from the main site of surgical dissection is preferred. By severing the anatomical structure as far as possible from the main surgical site as is surgically prudent, postoperative complications such as recurrent nerve entrapment are minimized. In addition, the positioning of the scissors in proximity to and then over the structure to be cut, and then the further movement of the scissors along the structure as far from the surgical site as determined to be prudent by the surgeon, and to the exclusion of any surrounding structure, must be carefully and unobtrusively accomplished. Thus, the proper use of surgical cutting instruments must provide for the optimal severance of the anatomical structure as far away from the main surgical site as is practical and clinically indicated in order to decrease the chances for post-operative complications such as symptomatic soft tissue structure entrapment within the area that defines the most concentrated operative scarring.

Thus, the prior art discloses a number of surgical cutting instruments, prominent among them are the Steinberg et al. patent (U.S. Pat. No. 5,746,748) that discloses a circumcision instrument that includes pivotally interconnected cross members that includes handles with finger loops at a proximal end jaws at a distal end with the jaws having surfaces that contact and clamp tissue therebetween for severing.

The Wales patent (U.S. Pat. No. 5,800,449) discloses a knife shield for surgical instruments that includes a handle from which a tube extends and which encloses therein a tissue stop for protecting tissue engaged by the jaws of the forceps until the surgeon desires to cut the tissue.

The Eubanks, Jr. et al. patent (U.S. Pat. No. 5,593,420) discloses a miniature endoscopic surgical instrument assembly and method of use that includes a securing mechanism for securing a miniature medical implement member to a support sheath so that the support sheath strengthens the implement member and prevents the implement member from breaking during an endoscopic medical procedure.

Nonetheless, despite the ingenuity of the above devices, there remains a need for a surgical cutting instrument having ergonomic handles that are offset from the main working axis of the instrument and which includes various operational handle positions and cutting jaws that cut in a plane normal to the main axis of the instrument and which are movable concomitant with the movement of the handles to the various positions for properly orienting and aligning the instrument with respect to the anatomical structure before cutting the structure.

SUMMARY OF THE INVENTION

The present invention comprehends co-axial actuated scissors for cutting anatomical structures, such as nerves, in a plane that is normal (at 90 degrees) to the primary working or operational axis of the scissors, with the working or operational axis extending from the base of the manually operable scissor handles and through rotatable cylindrical members to the cutting jaws wherein the concentric rotation of the cylindrical members relative to each other actuates the cutting action of the cutting jaws.

Thus, the co-axial actuated scissors include a first scissor portion slidably and telescopically securable to a second scissor portion. The first scissor portion includes an offset handle attached to a stem with an inner cylindrical rotatable member connected to the lower end of the stem. The inner cylindrical rotatable member defines a distal or loop end that includes an arcuate cutting blade or jaw. Formed on the stem is a receiving notch that opens rearwardly or away from the distal end that defines the location of the cutting jaw.

The co-axial actuated scissors also include a second scissor portion that includes an offset handle attached to a stem with the stem being attached at its lower end to a primary cylinder. The area where the stems of the handles for both the first and second scissor portions attach, respectively, to the inner rotatable member and the primary cylinder, is designated as the handle base. The primary cylinder includes a bore that is coequal in length with the primary cylinder and a longitudinal slot that is substantially coequal in length with the primary cylinder. An angulated or curved groove is located at the rear of the primary cylinder and in the area where the stem attaches to the primary cylinder, and, furthermore, the angulated groove registers with the longitudinal slot but is oriented transverse to the longitudinal slot. The primary jaw also defines a distal, cutting or loop end that includes an arcuate cutting blade or jaw that cooperates with the cutting blade mounted to the distal end of the inner cylindrical rotatable member for holding and severing the anatomical structure such as the nerve. Thus, more particularly, the position of the cooperating cutting jaws is denoted as the loop end of the scissors.

In addition, the second scissor portion includes an arcuate arm that extends from the stem toward, and depending upon the handle positions during use of the device, past the stem of the first scissor portion. The arcuate arm includes at least two spaced-apart detents that face the loop end of the scissors, and the detents are dimensioned to seat within the receiving notch concomitant with the surgeon moving the handles to the various operative surgical positions. Thus, the detents are spaced on the arm of the second scissor portion to provide for three discrete scissor positions (which also corresponds to the positions of the cutting jaws): a full open position, a surgical structure gripping position, and a cutting or severing position.

In assembling the co-axial actuated scissors the inner cylindrical rotating member of the first scissor portion is telescoped within the bore of the primary cylinder of the second scissor portion so that the inner member is rotatable within the bore and concentric thereto, and the cutting jaws are disposed in opposed cutting relationship at the loop end. The lower end of the stem of the first scissor portion seats within the angulated groove at the rear of the primary cylinder and travels within—and is delimited by—the length of the angulated groove during manipulation of the co-axial actuated scissors during the positioning, gripping and cutting of the anatomical structure. The inner member and the primary cylinder are disposed concentric relative to each other and define a longitudinal axis extending through the scissors from the handle end to the loop end. Furthermore, the cutting plane of the jaws—and thus the cutting action of the jaws—is normal (at 90 degrees) to the longitudinal axis and thus the axis of rotation of the inner member and the primary cylinder. In addition, the concentric rotatable disposition of the inner rotating member within the primary cylinder defines an axial length or portion that extends, in effect, from the handle end to the loop end, and the inner member and the primary cylinder rotate with respect to each other along this axial length. The stem of the second scissor portion is aligned with the receiving notch formed on the stem of the first scissor portion and moves through the receiving notch simultaneous with the manual movement of the offset handles to the various surgical positions. In addition, as the stem moves through the receiving notch the detents successively engage a cavity formed within the receiving notch thereby allowing the cutting jaws to be held and maintained in the full open position and the gripping position as long as desired by the surgeon. Completely closing the offset handles together causes the cutting jaws to sever the anatomical structure. The handles, and more specifically the finger holes of the handles, are disposed offset or non co-planar to the longitudinal axis and the disposition and cutting action of the jaws. Moreover, the offset finger holes of the handles enhance both the ease of use and the ergonomic functioning of the scissors.

There are several alternative embodiments that provide for the concentric rotation of the inner member relative to the primary member, but employ different structural elements to hold the cutting jaws in the various operational positions. In one alternative embodiment a protrusion extends from the surface of the inner cylinder at the rear thereof. Formed on the inner annular surface of the primary cylinder, and in alignment with the protrusion, is a plurality (preferably three) of spaced-apart notches each of which is sized to receive the protrusion. The notches are spaced on the inner annular surface of the primary cylinder in an arcuate arrangement so as to define the various surgical operative positions for the scissors, i.e., the fully open position, the anatomical structure gripping position and the cutting position. Thus, as the surgeon manipulates and opens and closes the handles, the inner member and the primary cylinder rotate relative to each other concomitant with the protrusion seating in the notch with each notch corresponding to a discrete surgical position. The surgical positions correspond to the surgeon first positioning the scissors adjacent the structure to be cut, then gripping the structure at the loop end and sliding the scissors along the structure for positioning and placing the loop end at the desired orientation, and as far from the surgical site as determined to be prudent by the surgeon, and then closing the cutting jaws for severing the anatomical structure such as the nerve.

It is an object of the present invention to provide co-axial actuated scissors that include indicia or markings that are calibrated for measuring the distance from the surgical site at which the cut is being made to the base of the handles of the scissors.

It is another object of the present invention to provide co-axial actuated scissors that can capture and sever structures that can vary by site and application.

It is yet another object of the present invention to provide co-axial actuated scissors wherein the cutting is accomplished at an orientation that is normal to the longitudinal axis of the scissors.

It is still yet another object of the present invention to provide co-axial actuated scissors that allow a surgeon to move along a nerve or other structure to be severed to a surgically optimum position into the operative wound while continuously maintaining contact with the nerve or other structure.

It is still yet a further object of the present invention to provide co-axial actuated scissors wherein the cutting blades of the scissors produce a clean and complete cut without fraying of the anatomic surgical structure.

A further object of the present invention is to provide co-axial actuated scissors that include cutting blades that are inwardly bent toward each other thereby increasing the binding forces of the blades in order to produce a clean severance of the anatomical surgical structure.

A still further object of the present invention is to provide co-axial actuated scissors that achieve the cutting of the anatomical surgical structure without cutting any adjacent structure and without direct visualization of the particular anatomical surgical structure that is being cut.

Still another object of the present invention is to provide co-axial actuated scissors that allow the surgeon to cut the nerve or other structure as far as possible from the main surgical site thereby minimizing post-operative complications.

Still yet another object of the present invention is to provide co-axial actuated scissors wherein all dimensions, including the shapes of the handles, can be variable depending upon different applications and surgical sites.

Still yet a further object of the present invention is to provide co-axial actuated scissors wherein the attachment and detachment of the handle portions is by a slidable telescoping action that doesn't require screws or other fixation devices and which allows for easy reprocessing and sterilization of the instrument after usage.

Yet another object of the present invention is to provide co-axial actuated scissors that are manufactured from a medical-grade stainless steel or other premium alloy.

Yet still another object of the present invention is to provide co-axial actuated scissors that are capable of being used in the sectioning or freeing of tendons during amputations or tendon transfer procedures.

Yet still a further object of the present invention is to provide co-axial actuated scissors wherein the cutting blades form a capturing loop that captures the anatomical surgical structure and allows the scissors to slide proximally and distally along the anatomical structure until the desired position is obtained at which time the handles can be completely closed thereby closing the cutting blades and causing the anatomical surgical structure to be cut and severed.

These and other objects, features and advantages will become apparent to those skilled in the art upon a perusal of the following detailed description read in conjunction with the accompanying drawing figures and appended claims.

BRIEF DESCRIPTION OF THE DRAWINGS

FIG. 9 is a front elevational view of the co-axial actuated scissors of the present invention illustrating the engagement of the first detent with the stem and the disposition of the handles and the cutting jaws when the scissors are disposed to the open position;

FIG. 10 is a front elevational view of the co-axial actuated scissors of the present invention illustrating the engagement of the second detent with the stem and the disposition of the handles and the cutting jaws when the scissors are disposed to the anatomical structure gripping position;

FIG. 11 is a front elevational view of the co-axial actuated scissors of the present invention illustrating the closing of the handles and the concomitant closing of the cutting jaws for cutting and severing the anatomical structure such as the nerve;

FIG. 12 is a side elevational view of the co-axial actuated scissors of the present invention illustrating the orientation of the offset handles relative to the cutting jaws that are normal to the main longitudinal axis of the scissors;

DETAILED DESCRIPTION OF THE PREFERRED EMBODIMENT

Figure 1:
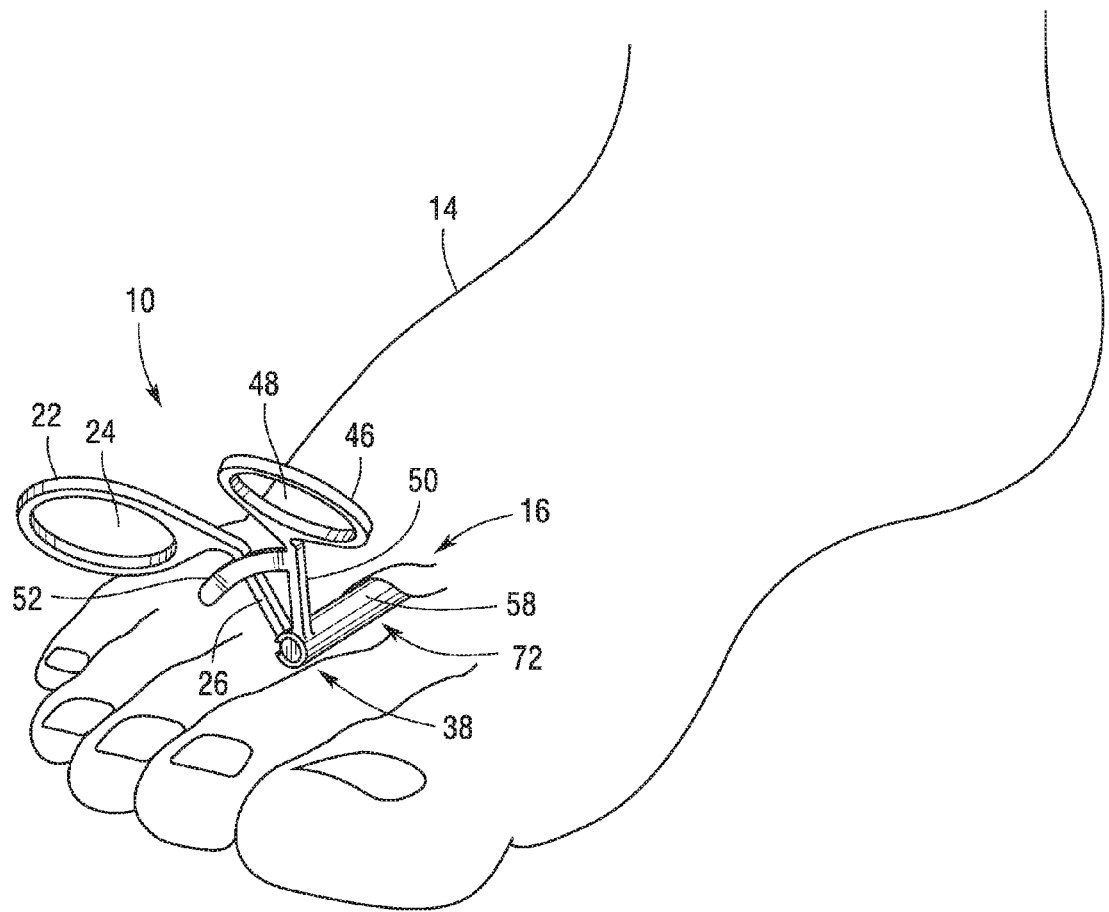
FIG. 1 is a perspective view of the co-axial actuated scissors of the present invention illustrating the disposition of the co-axial actuated scissors for cutting an anatomical structure in the foot of the individual.

Illustrated in FIGS. 1 through 28 are several embodiments for co-axial actuated scissors whose primary working action is through two concentric members that rotate with respect to each other along a main longitudinal axis that extends from an operating hand position to a distal, loop or cutting end. Moreover, the capturing, holding and cutting of an anatomical structure, such as a nerve, is done normal (perpendicular or at 90 degrees) to the main longitudinal axis. In addition, the operation of the scissors is such that the handles can be squeezed for reaching an initial operational position so that the cutting end of the scissors can be appropriately positioned proximally or distally relative to the anatomical structure, with the handles then being closed for cutting and severing the anatomical structure.

Thus, shown in FIGS. 1 through 18 is a preferred embodiment for co-axial actuated scissors 10 for cutting anatomical structures, such as a nerve 12, extending through the foot 14 of an individual with the cutting of nerve 12 occurring away from the surgical site 16 and without harming adjacent tissue or the need for making a second incision. Scissors 10 of FIGS. 1 through 18 includes a pair of coacting scissor portions; more specifically denoted a first scissor portion 18 and a second scissor portion 20. As will be hereinafter further described, first scissor portion 18 is slidably and telescopically disposed in second scissor portion 20 so that both scissor portions 18 and 20 can concentrically rotate relative to each other for effecting the holding and then the cutting of nerve 12. First scissor portion 18 includes a first offset handle 22 and a finger hole 24 defined by circular offset handle 22. A stem 26 is integrally attached to the lower portion of offset handle 22, and stem 26 includes a rearwardly formed rectangular-shaped receiving notch 28. Moreover, as shown most clearly in FIG. 7b, receiving notch 28 is further defined by a detent cavity 30 that is smaller than receiving notch 28 and generally centrally located thereon.

As shown in FIGS. 1 through 18, stem 26 includes a lower end 32, and lower end 32 of stem 26 is integrally connected to an elongated inner first concentric member or cylindrical rotating member 34. Inner cylindrical rotating member 34 preferably is a solid structure or piece, and the area where lower end 32 of stem 26 attaches to inner rotating member 34 is defined as the rear or handle end 36 of first scissor portion 18. This area can also be referred to as the proximal end 38 of first scissor portion 18 and, by extension, scissors 10. Opposite of handle end 36 is a distal end 40 of first scissor portion 18, and located at distal end 40 is an arcuate cutting blade or jaw 42 terminating with a jaw or blade tip 44.

Coacting with and slidably and telescopically engaged to first scissor portion 18 is second scissor portion 20 as shown in FIGS. 1 through 18. Second scissor portion 20 includes a second offset handle 46, and cylindrical offset handle 46 defines a finger hole 48. A stem 50 is attached to the lower portion of offset handle 46, and laterally extending from stem 50 is an arcuate arm 52 that is appropriately sized to pass through receiving notch 28 on first scissor portion 18 during operation of scissors 10. Arm 52 includes a detent means that includes a plurality of stops or detents forwardly facing for determining the various surgical operational positions of the handle by their successive and discrete engagement and seating within cavity 30 of receiving notch 28. As shown in FIGS. 1 through 18, the preferred embodiment of the invention includes at least two detents 54 denoted the initial or first detent and the second detent, and the successive and discrete engagement of each detent 54 with receiving notch 28 denotes a specific scissor position or configuration as will be hereinafter further explained.

Figure 5:
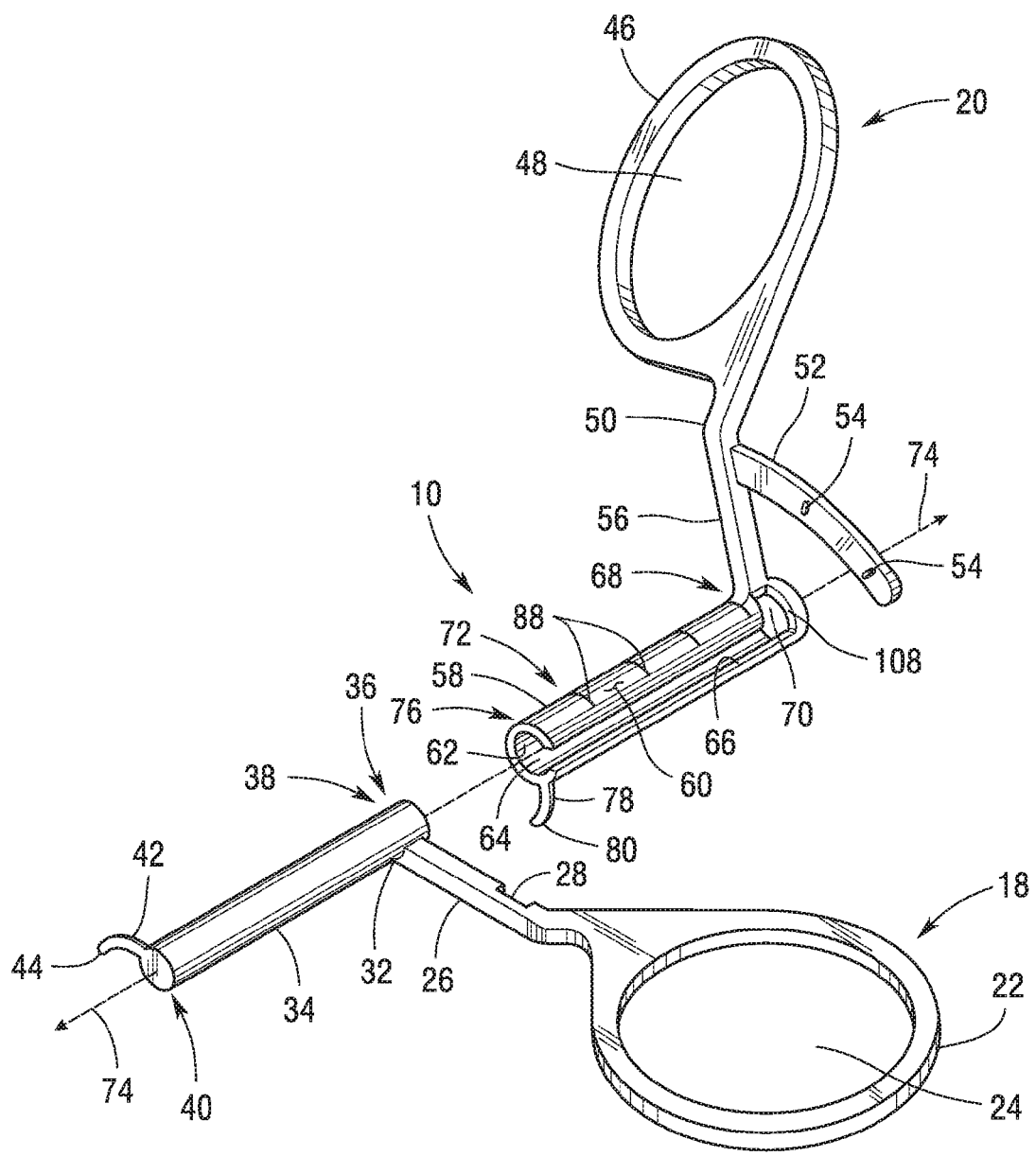
FIG. 5 is a perspective view of the co-axial actuated scissors of the present invention illustrating the disassembly of the scissors and the structural elements that comprise the first scissor portion and the second scissor portion.
Figure 6:
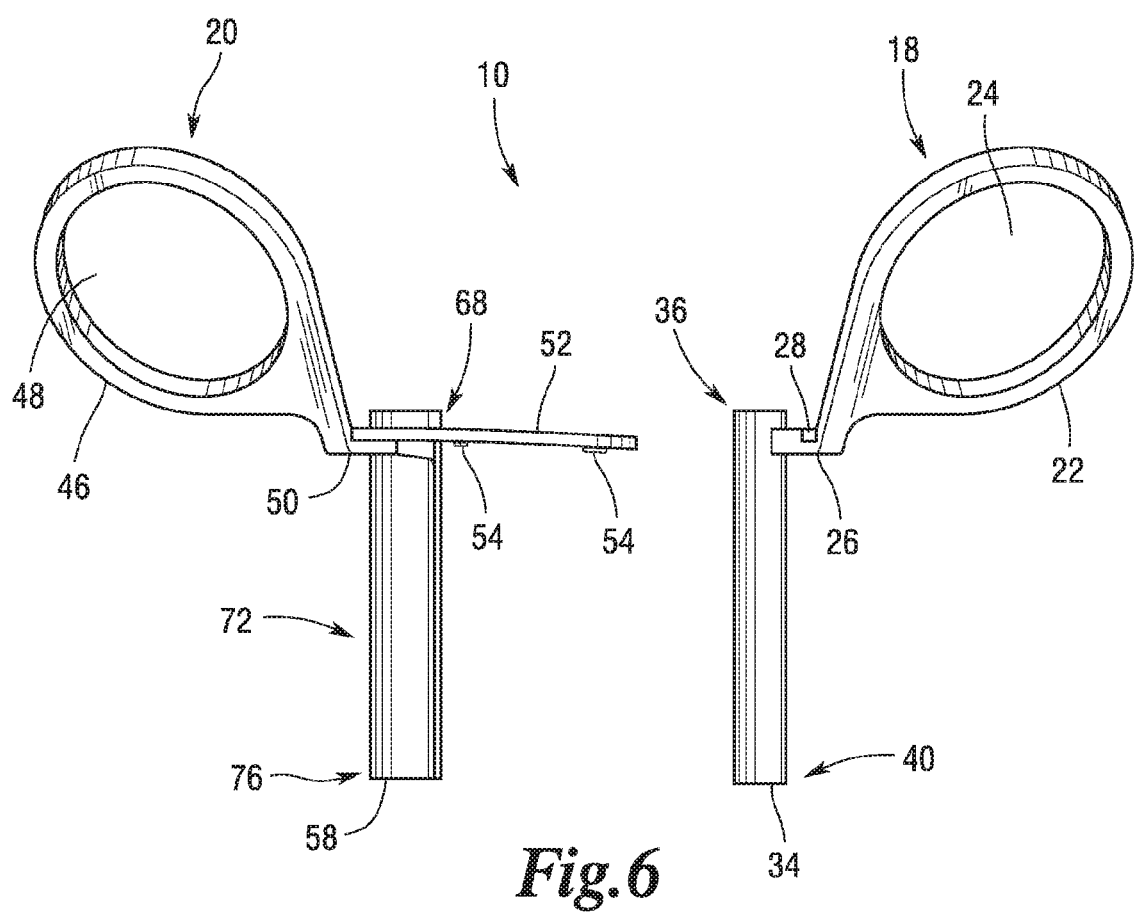
FIG. 6 is a top plan view of the co-axial actuated scissors of the present invention illustrating the first scissor portion disassembled from the second scissor portion.
Figure 7A:
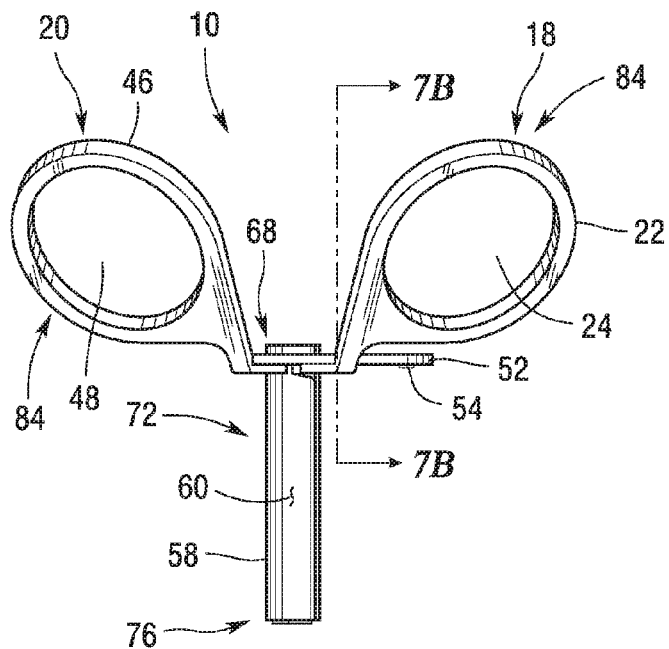
FIG. 7a is a top plan view of the co-axial actuated scissors of the present invention illustrating the location of the handles when the scissors are disposed to the gripping position for sliding along and holding the anatomical structure.
Figure 7B:
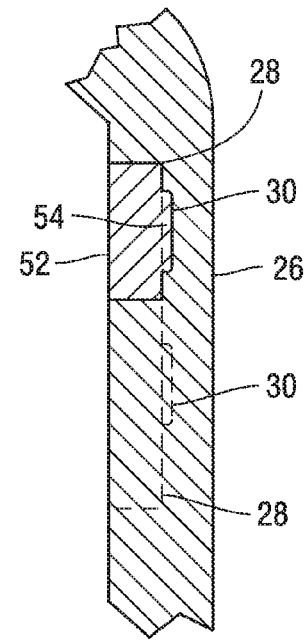
FIG. 7b is a sectioned side elevational view of the co-axial actuated scissors of the present invention taken along lines 7b-7b of FIG. 7a illustrating the engagement of the detent on the arm of the second scissor portion with the receiving notch of the stem of the first scissor portion.
Figure 7C:
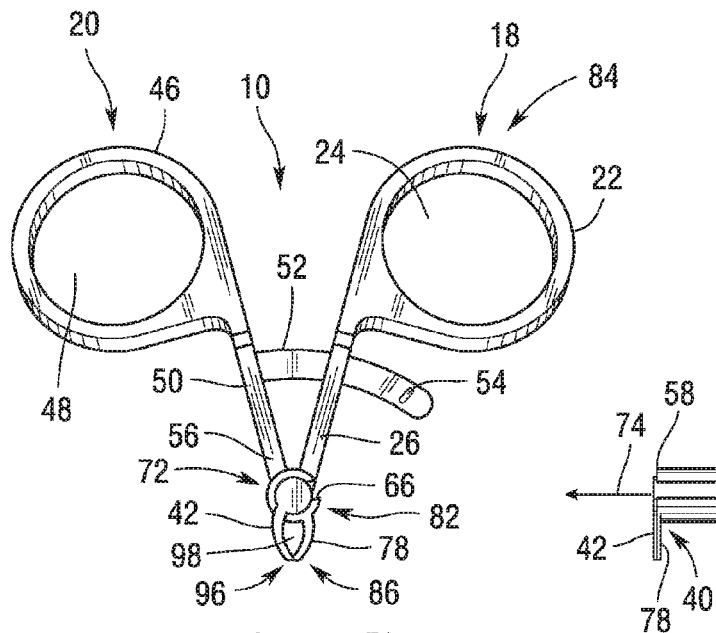
FIG. 7c is a front elevational view of the co-axial actuated scissors of the present invention illustrating the position of the handles and the cutting jaws when the scissors are disposed to the anatomical structure gripping position.
Figure 7D:
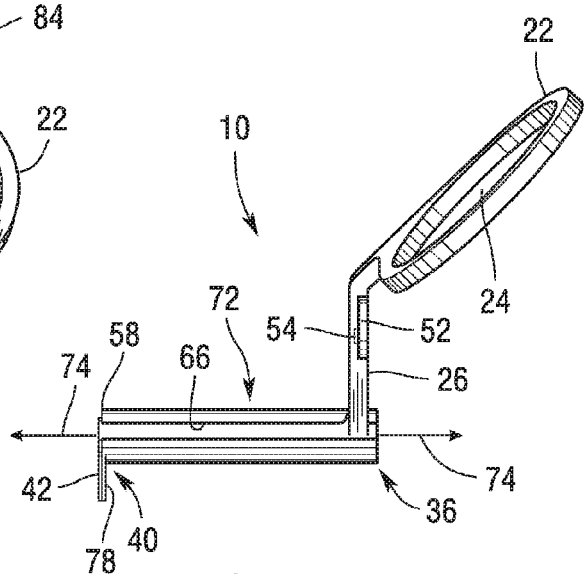
FIG. 7d is a side elevational view of the co-axial actuated scissors of the present invention illustrating the offset orientation of the handles relative to the longitudinal main axis of the scissors and the projection of the cutting jaws normal to the longitudinal axis.

Lower end 56 of stem 50 of second scissor portion 20 attaches to an elongated second outer concentric member or primary cylinder 58 that is slightly longer than inner rotating member 34 of first scissor portion 18. Primary cylinder 58 includes an annular external surface 60 and an inner annular surface 62. Primary cylinder 58 includes a bore 64 coequal in length with primary cylinder 58 and a longitudinal slot or groove 66 that extends through the surface of primary cylinder 58 and which substantially extends along the length of primary cylinder 58. Located at the rear or handle end 68 of second scissor portion 20 is an angulated or proximal groove 70. Angulated groove 70 extends transverse to longitudinal slot 66 but opens and joins to longitudinal slot 66; and thus slot 66 and angulated groove 70 form, in effect, a continuous opening on primary cylinder 58. In addition, the width of longitudinal slot 66 is slightly greater than stem 26 of first scissor portion 18 for facilitating the assembly of first scissor portion 18 to second scissor portion 20 as will be hereinafter explained. Thus, body 72 of scissors 10 comprises both inner rotating member 34 and primary cylinder 58 when they are assembled together for concentric rotation relative to each other during the operation of scissors 10. It should also be noted that body 72 of scissors 10 defines a main longitudinal axis 74 extending therethrough (through inner rotating member 34 and primary cylinder 58), and this axis 74 is indicated in FIGS. 5 and 7d. Handles 22 and 46 are thus offset or angled from axis 74 at an angle that is between 0 degrees and 90 degrees as shown in FIG. 7d (handles 22 and 46 are offset at approximately 45 degrees in FIG. 7d), and this offset enhances the ease and use of scissors 10 during the surgical procedure. The rotation of inner rotating member 34 and primary cylinder 58 is about this main longitudinal axis 74. As with inner rotating member 34, opposite of handle end 68 of second scissor portion 20 is a distal end 76, and, more specifically, located at distal end 76 and integrally formed on and extending from primary cylinder 58 is an arcuate cutting jaw or blade 78. Cutting blade 78 includes a blade tip 80, and cutting blade 78 of second scissor portion 20 is inwardly curved relative to cutting blade 42 of first scissor portion 18 to achieve maximum shearing force for cleanly and quickly severing the anatomical structure when cutting jaws 42 and 78 are closed upon each other as shown, for example, in FIGS. 8c, 11, and 13. The distal end 76 of body 72 of scissors 10 is also denoted the cutting or loop end 82, and this denotes to the configuration cutting jaws 42 and 78 take during the use of scissors 10, especially when cutting jaws 42 and 78 are disposed to a particular detent position to be hereinafter further explained.

With reference to FIGS. 5 through 14, cutting jaws 42 and 78 extend from body 72 of scissors 10 and are disposed normal to main longitudinal axis 74 of scissors 10 while handles 22 and 46 are offset or angled with regard to main longitudinal axis 74 and the extension of cutting jaws 42 and 78. Handles 22 and 46 define an operating hand position 84 and cutting jaws 42 and 78 define a cutting position 86 with inner rotating member 34 and primary cylinder 58 (body 72 of scissors 10) rotating relative to each other and about main longitudinal axis 74. The co-operative pivotal movement and cutting action of cutting jaws 42 and 78 occurs concomitant with the rotation of concentrically disposed rotating member 34 and primary cylinder 58 and in a plane normal to their concurrent concentric rotation. Cutting position 86 may be fully open position 94, gripping position 96, or surgical cutting position 100, as more fully described herein.

Figure 2:
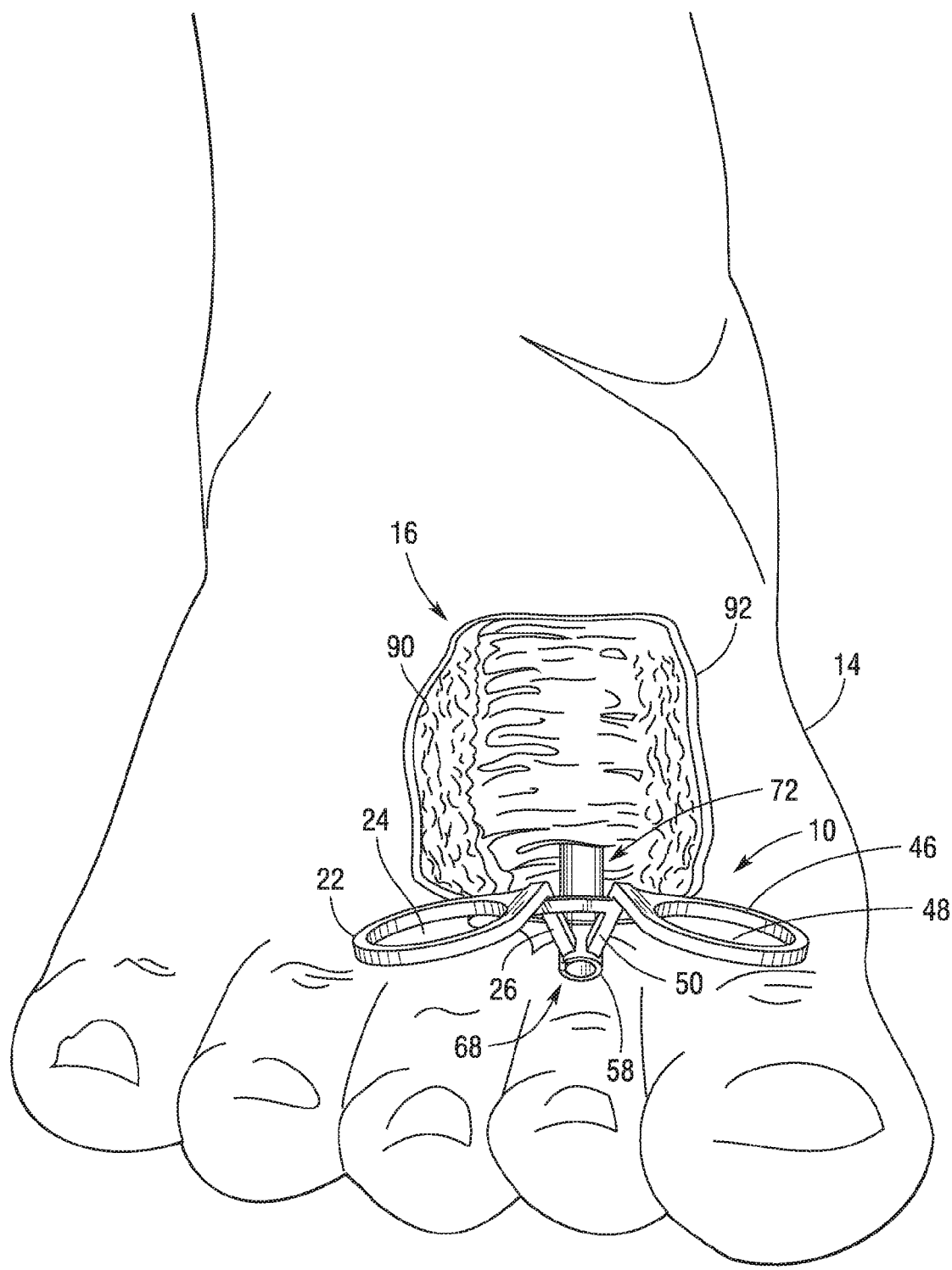
FIG. 2 is a front elevational view of the co-axial actuated scissors of the present invention illustrating the disposition of the scissors as the scissors are slid along the structure to achieve the proper orientation and position before the severing of the anatomical structure.

As shown in FIG. 5, the upper part of external surface 60 of primary cylinder 58 is calibrated with regularly spaced indicia or markings 88 for measuring and determining the distance from surgical site 16 at which the anatomical structure is being cut to the point, place or depth of insertion of body 72 of scissors 10. Thus, as shown in FIGS. 1 and 2, body 72 of scissors 10 has been inserted beneath upper layers 90 of skin 92 of foot 14 and into foot 14 for positioning and holding the anatomical structure. Regularly spaced indicia 88 allows the surgeon to determine how far into foot 14 body 72 of scissors 10 extends without the need for direct visualization and without the need for lifting up the various layers 90 of skin 92, muscle and tissue surrounding surgical site 16.

Figure 8A:
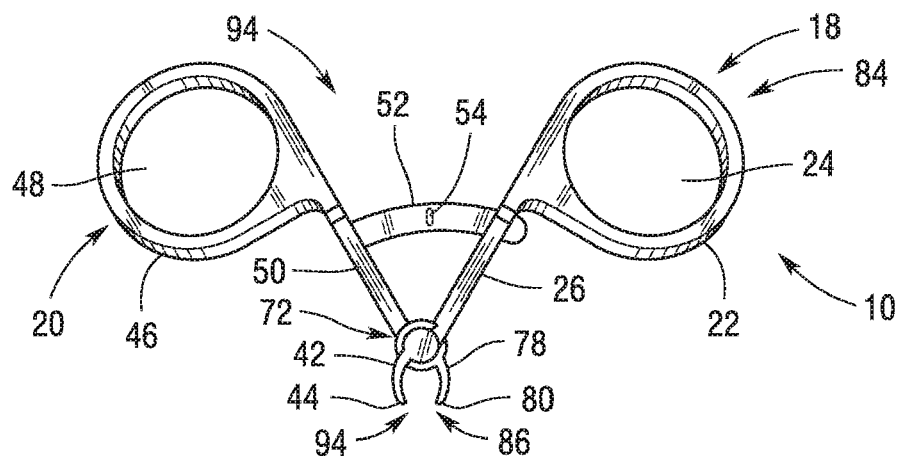
FIG. 8a is a front elevational view of the co-axial actuated scissors of the present invention illustrating the engagement of the first detent with the receiving notch on the stem of the first scissor portion for maintaining the scissors in the fully open disposition.
Figure 8B:
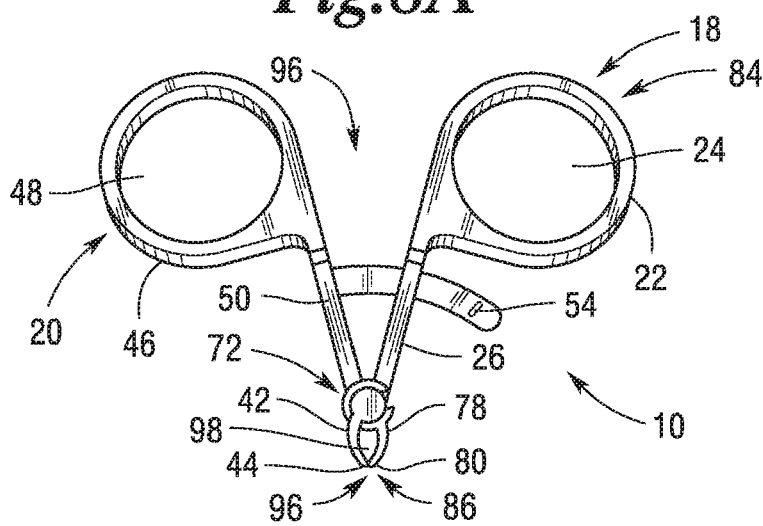
FIG. 8b is a front elevational view of the co-axial actuated scissors of the present invention illustrating the engagement of the second detent with the receiving notch of the stem of the first scissor portion and the formation of an aperture by the cutting jaws for holding the anatomical structure and maintaining the scissors in the gripping position.
Figure 8C:
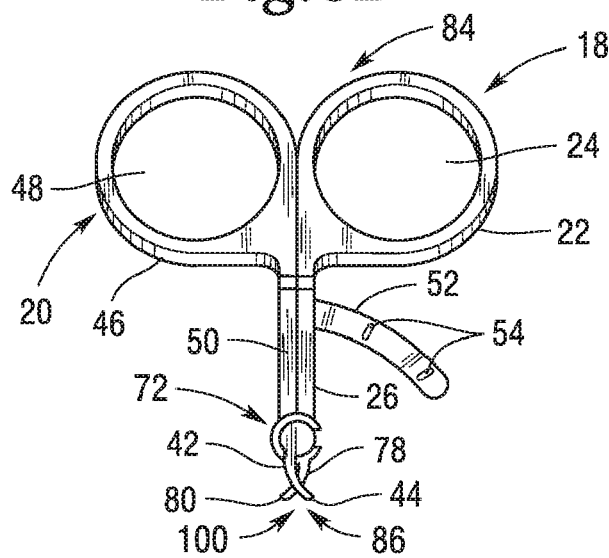
FIG. 8c is a front elevational view of the co-axial actuated scissors of the present invention illustrating the closing of the handles upon each other and the concomitant movement of the cutting jaws to the maximum cutting position for severing the anatomical structure.
Figure 13:
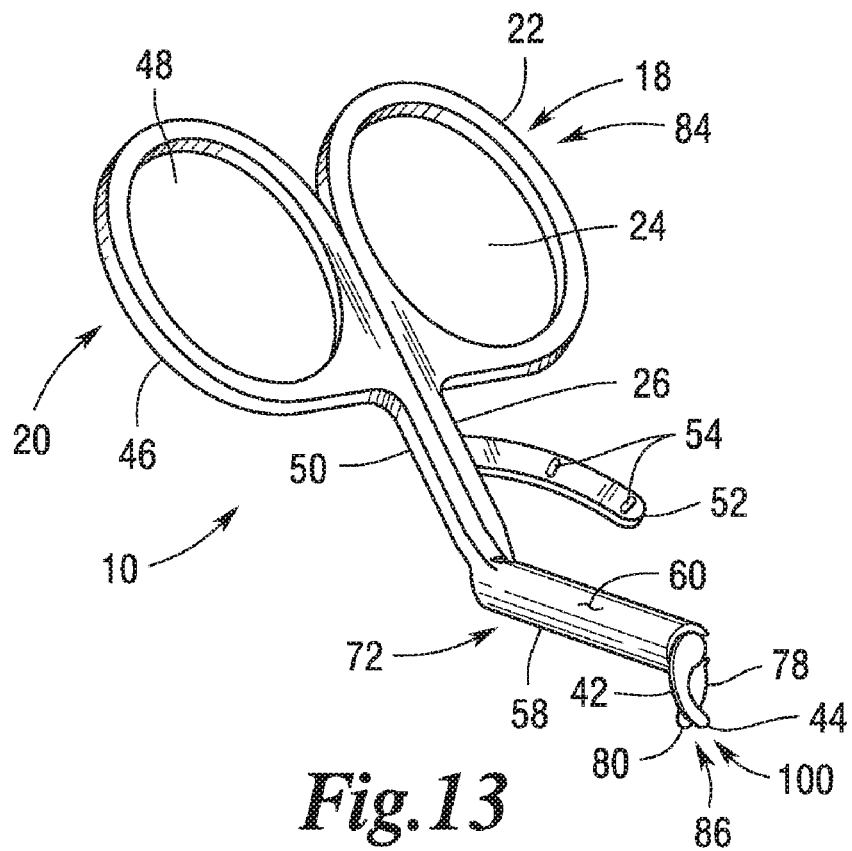
FIG. 13 is a perspective view of the co-axial actuated scissors of the present invention illustrating the closing together of the handles and the concomitant closing of the cutting jaws.
Figure 14:
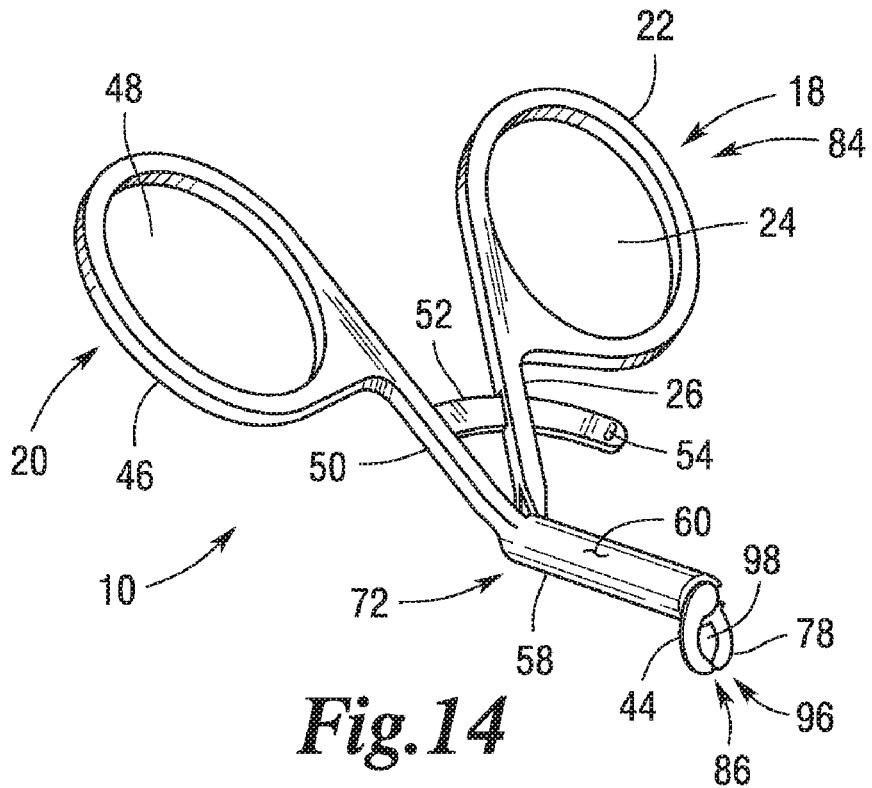
FIG. 14 is a perspective view of the co-axial actuated scissors of the present invention illustrating the engagement of the second detent with the stem and the disposition of the jaws at the anatomical structure gripping position.
Figure 15:
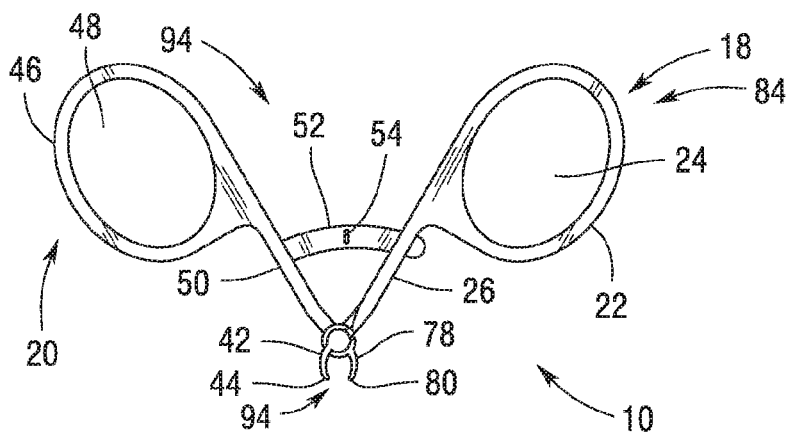
FIG. 15 is a front elevational view of the co-axial actuated scissors of the present invention illustrating the disposition of the handles and the cutting jaws when the scissors are at the fully open position.
Figure 16:
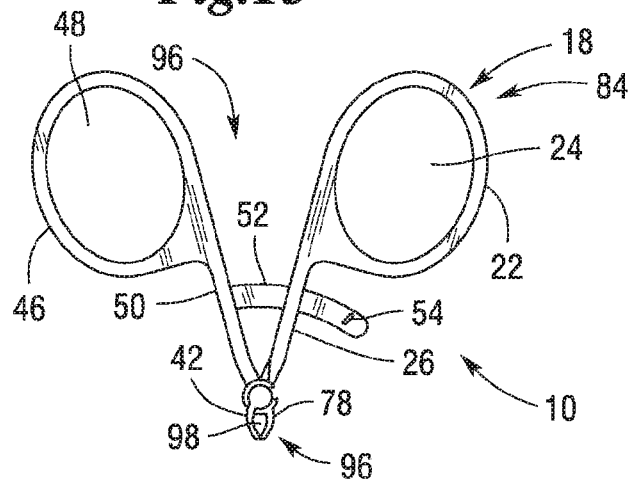
FIG. 16 is a front elevational view of the co-axial actuated scissors of the present invention illustrating the disposition of the handles and the cutting jaws when the scissors are at the anatomical structure gripping position.
Figure 17:
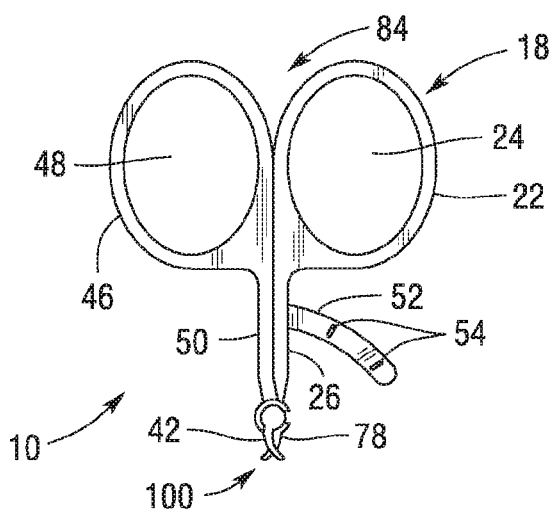
FIG. 17 is a front elevational view of the co-axial actuated scissors of the present invention illustrating the disposition of the handles and the cutting jaws when the scissors are closed for cutting and severing the anatomical structure.
Figure 18:
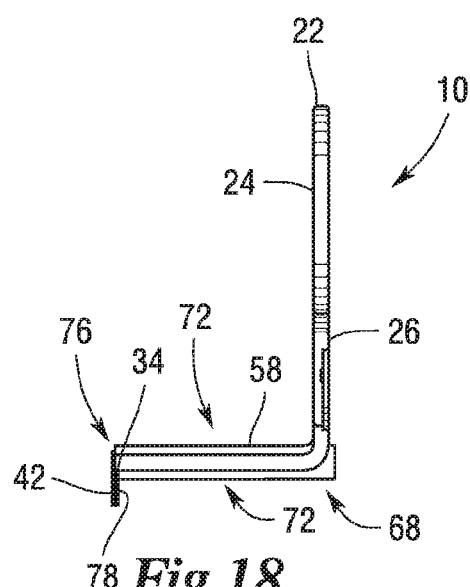
FIG. 18 is a side elevational view of the co-axial actuated scissors of the present invention illustrating the disposition of the handles and the jaws as being normal to the longitudinal main axis of the scissors.
Figure 19:
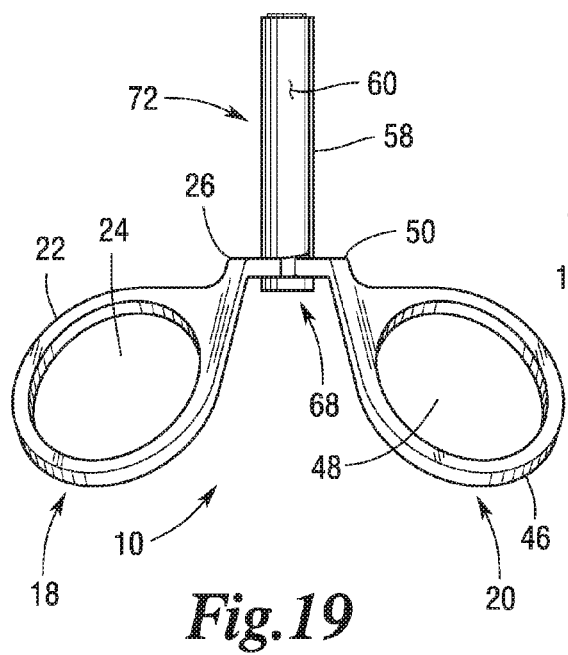
FIG. 19 is a top plan view of a first alternative preferred embodiment of the co-axial actuated scissors of the present invention.

As shown in FIGS. 8a through 8c, 9 through 11 and 15 through 17, scissors 10 have three distinct operational detent positions wherein the manual movement of handles 22 and 46 causes the successive engagement of detents 54 with receiving notch 28 and the concomitant rotation of rotating member 34 and primary cylinder 58 causing the pivotal movement of cutting jaws 42 and 78. Fully open position 94 is shown in FIGS. 8a, 9 and 15, and in fully open position 94, detent 54 denoted first detent has engaged receiving notch 28 and the end of arm 52 of second scissor portion 20 projects slightly past receiving notch 28 and stem 26 of first scissor portion 18. Cutting jaws 42 and 78 of scissors 10 are fully open to allow the surgeon to initially orient and dispose scissors 10 with respect to surgical site 16 and the anatomical structure to be cut. Anatomical structure gripping position 96 is shown in FIGS. 8b, 10 and 16, and to obtain this position, handles 22 and 46 are closed upon each other thereby causing the concurrent concentric rotation of rotating member 34 and primary cylinder 58 and bringing cutting tips 44 and 80 of jaws 42 ad 78 into engagement. Arm 52 of second scissor portion 20 slides within receiving notch 28 of first scissor portion 18 until detent 54 denoted the second detent is encountered, and upon encountering this second detent, a slight resistance to further movement results and this detent seats within receiving notch 28 thereby maintaining the anatomical structure gripping position. With tips 44 and 80 of cutting jaws 42 and 78 touching each other, an arcuate shape for jaws 42 and 78 forms, in effect, the loop configuration that defines loop end 82, and the loop configuration includes an aperture 98 that encompasses and holds the anatomical structure, such as nerve 12 therein and between cutting jaws 42 and 78 prior to the cutting action. Scissors 10 can now be slid or pushed proximally or distally with nerve 12 contained and held within aperture 98 as far from surgical site 16 as determined prudent by the surgeon. Once satisfied with the placement and orientation of scissors 10—and particularly the placement of cutting jaws 42 and 78—the next detent position is obtained. Thus, FIGS. 8c, 11 and 17 illustrate the detent or surgical cutting position 100 produced by handles 22 and 46 coming together at the limit of the rotational ability of inner rotating member 34 and primary cylinder 58. This limit also defines the pivotal range of motion of jaws 42 and 78. Simultaneous with the closure of handles 22 and 46 detent 54 denoted the second detent is disengaged from receiving notch 28 thereby allowing arm 52 to continue sliding through receiving notch 28. Concomitant with this action cutting blades 42 and 78 close upon and sever nerve 12. In severing nerve 12, which is shown most distinctly in FIG. 3b, cutting tips 44 and 80 of cutting blades 42 and 78 move past each other concomitant with the closure of handles 22 and 46 and the rotation of rotating member 34 concentric and relative to primary cylinder 58 for cleanly severing, and without fraying, the anatomical structure such as nerve 12. Angulated groove 70 delimits the rotation of first scissor portion 18 with respect to second scissor portion 20 and thus the movement of handle 22 and cutting blade 42 of first scissor portion 18 with respect to second scissor portion 20. After nerve 12 has been severed the surgeon would open scissors 10 by pivoting handles 22 and 46 away from each other, and thus the above described actions would all be repeated but in the reverse order.

Figure 3A:
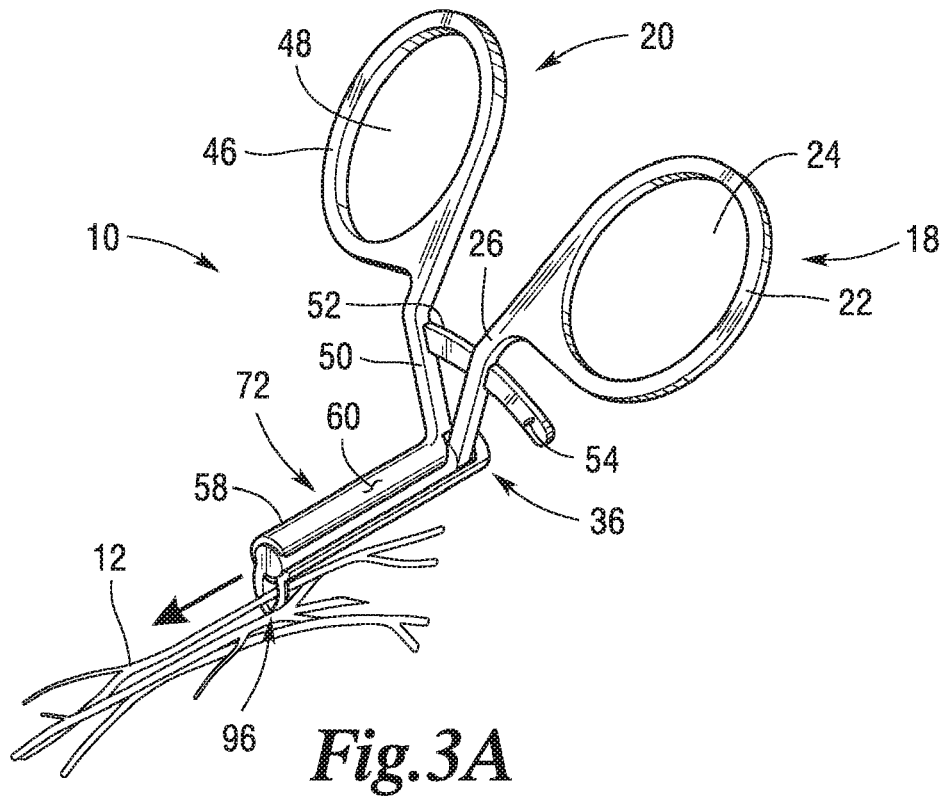
FIG. 3A is a perspective view of the co-axial actuated scissors of the present invention illustrating the engagement of one handle with a detent for holding the scissors at the gripping position resulting in the capturing of the anatomical structure by the loop end of the scissors.
Figure 3B:
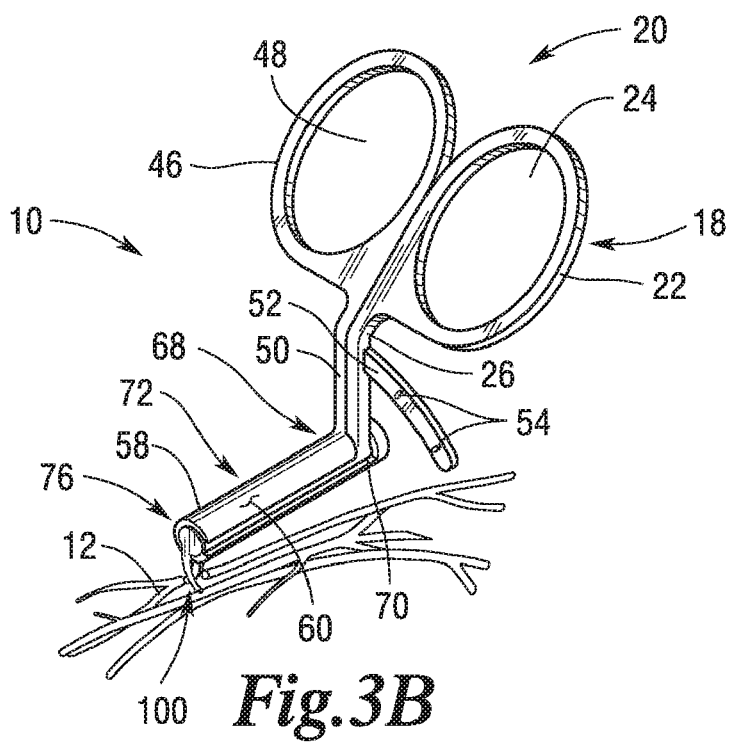
FIG. 3b is a perspective view of the co-axial actuated scissors of the present invention illustrating the closing of the handles and the concomitant axial rotation of the scissors thereby bringing the jaws together to sever the anatomical structure.
Figure 4A:
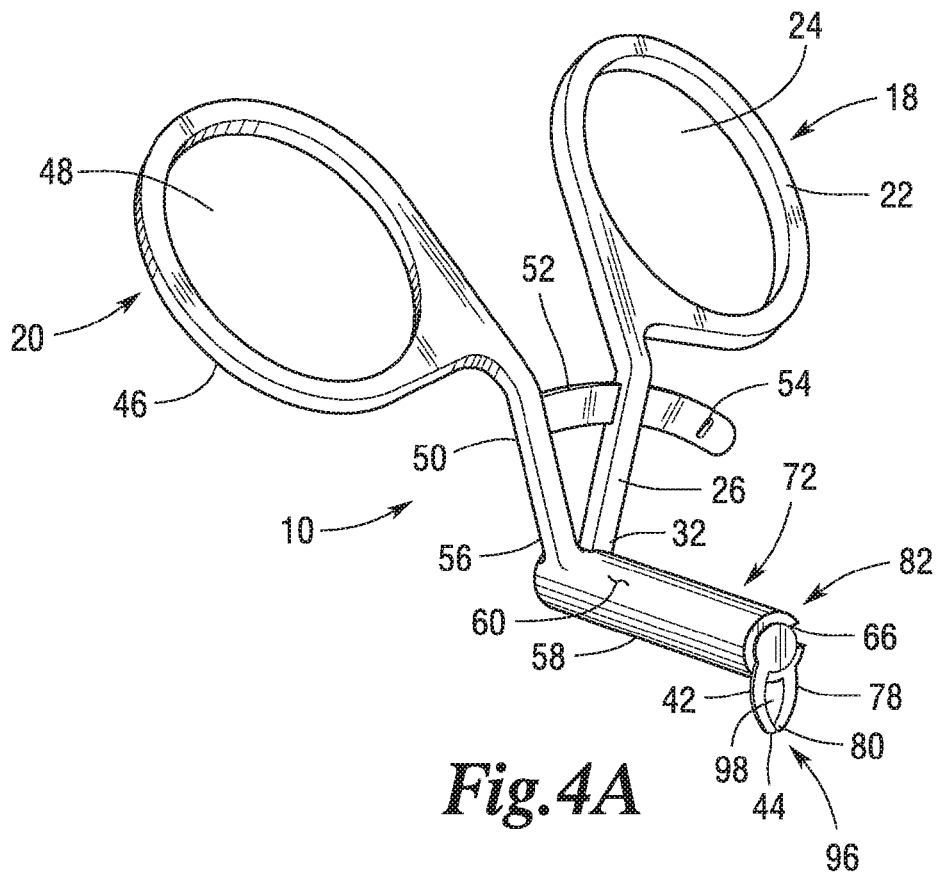
FIG. 4a is a perspective view of the co-axial actuated scissors of the present invention illustrating the engagement of the handles with the detent for maintaining the scissors at the gripping position and the cutting jaws oriented for holding the anatomical structure.
Figure 4B:
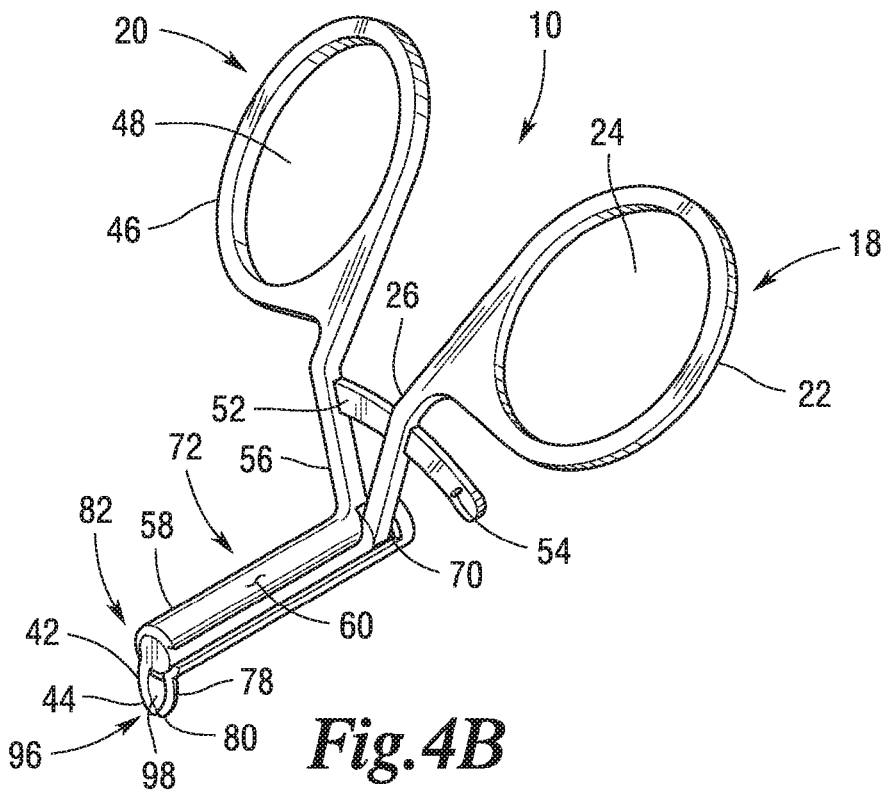
FIG. 4b is a perspective view of the co-axial actuated scissors of the present invention illustrating the disposition of the scissors at the gripping position, the movement of the stem of the handle of the first scissor portion within the angulated groove of the second scissor portion, and the aperture formed by the abutment of the cutting jaws for holding the anatomical structure.

With reference to FIGS. 1 through 18, a representative clinical use or application of scissors 10 would commence with both scissor portions 18 and 20 initially being placed on the surgical tray in an unassembled configuration. As shown in FIG. 5, in order to assemble first scissor portion 18 to second scissor portion 20, stem 26 of first scissor portion 18 is aligned with longitudinal slot 66 of primary cylinder 58 so that inner rotating member 34 can be telescopically slid within bore 64 of primary cylinder 58. Stem 26 of first scissor portion 18 would be received within angulated groove 70 of primary cylinder 58 for pivotal movement therein. Accompanying this placement would be the disposition of the tip of arm 52 of second scissor portion 20 within receiving notch 28 of first scissor portion 18. Handles 22 and 46 would be manually squeezed and moved toward each other so that detent 54 denoted the first detent would engage receiving notch 28 thereby disposing scissors 10 to fully open position 94. When passed to the surgeon, scissors 10 would be placed into proximity with and then over surgical site 16 and the structure, such as nerve 12 as shown in FIGS. 1 through 3b, that is to be severed. The surgeon would then manually squeeze and move handles 22 and 46 further toward each other so that detent 54 denoted the second detent encounters receiving notch 28 thereby simultaneously pivoting cutting jaws 42 and 78 toward each other for grasping, capturing and holding nerve 12 between cutting jaws 42 and 78. Upon obtaining anatomical structure gripping position 96 scissors 10 can then be pushed or slid proximally or distally along the anatomical structure, such as nerve 12, with jaws 42 and 78 encompassing nerve 12 and nerve 12 enclosed within aperture 98 to a position as far from surgical site 16 as determined to be prudent by the surgeon. The slidable movement of jaws 42 and 78 and body 72 of scissors 10, as shown in FIGS. 1 and 2, would be to the exclusion of any other surrounding structure. When the surgeon is satisfied with the orientation and placement of scissors 10—and crucially the position of cutting jaws 42 and 78—handles 22 and 46 are completely closed upon each other thereby causing the simultaneous disengagement of detent 54 denoted the second detent from receiving notch 28 and cavity 30, and the movement of jaws 42 and 78 toward each other for severing nerve 12 with cutting tips 44 and 80 of jaws 42 and 78 actually passing by each other as shown in FIGS. 3b and 8c as the cut is completed. Scissors 10 are then withdrawn from surgical site 16 along with the specimen generally with handles 22 and 46 reoriented so that detent 54 denoted the second detent is brought back into engagement with receiving notch 28. Scissors 10 can then be returned back to the surgical tray for reprocessing and sterilization in central supply.

Illustrated in FIGS. 19 through 28 are several alternative embodiments for scissors 10 shown in FIGS. 1 through 18. The alternative embodiments primarily disclose alternative detent structures for reaching, setting and maintaining the various surgical positions 94, 96 and 100 that result from the closing—or opening—of handles 22 and 46 and the simultaneous concentric rotations of inner rotating member 34 and primary cylinder 58.

Figure 20:
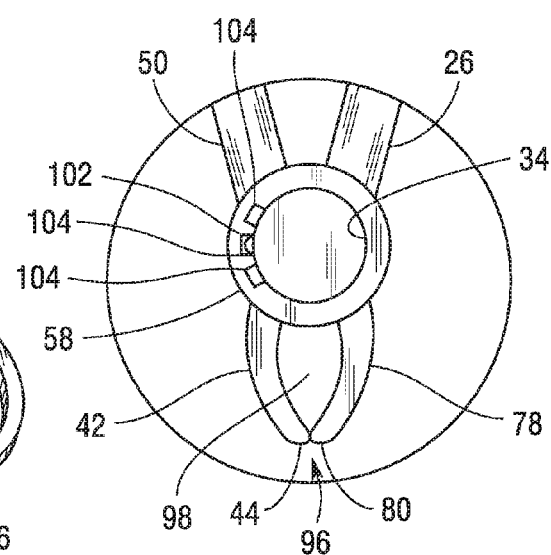
FIG. 20 is an enlarged front elevational view of the first alternative preferred embodiment of the co-axial actuated scissors of the present invention first shown in FIG. 19.
Figure 21:
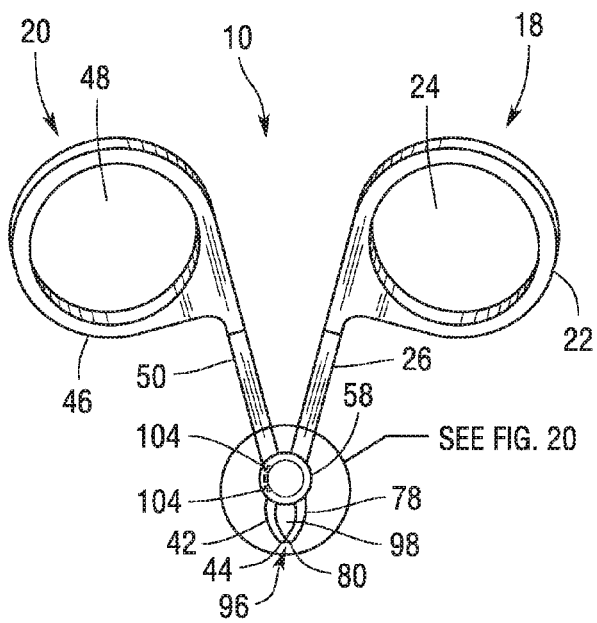
FIG. 21 is a front elevational view of the first alternative preferred embodiment of the co-axial actuated scissors of the present invention first shown in FIG. 19.
Figure 22:
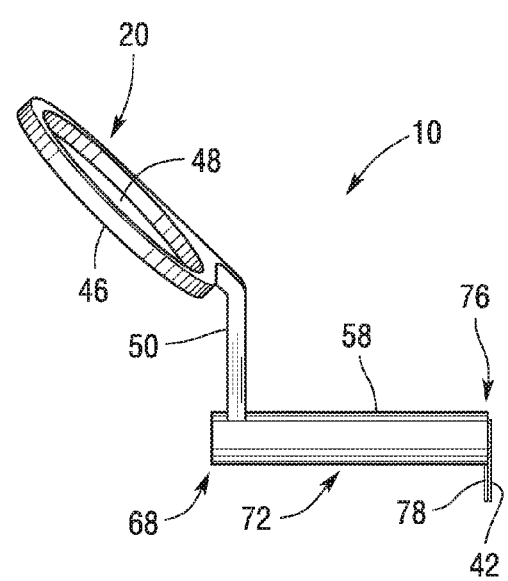
FIG. 22 is a side elevational view of the first alternative preferred embodiment of the co-axial actuated scissors of the present invention first shown in FIG. 19.
Figure 23:
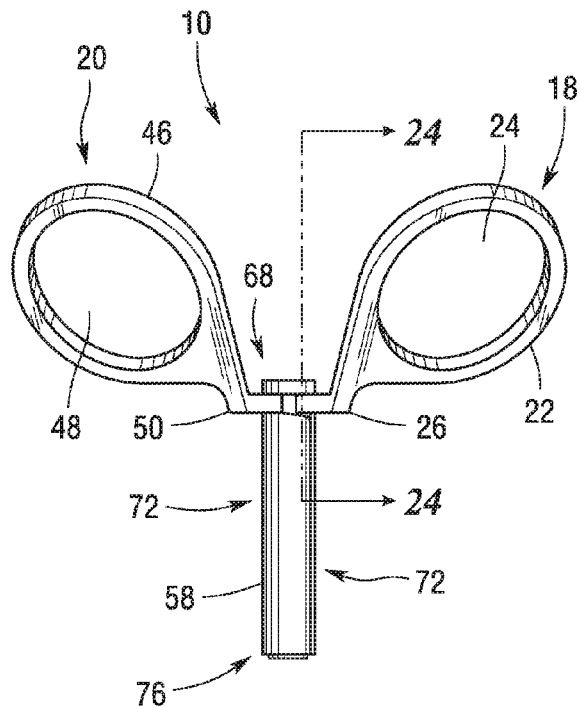
FIG. 23 is a top plan view of a second alternative preferred embodiment of the co-axial actuated scissors of the present invention.
Figure 24:
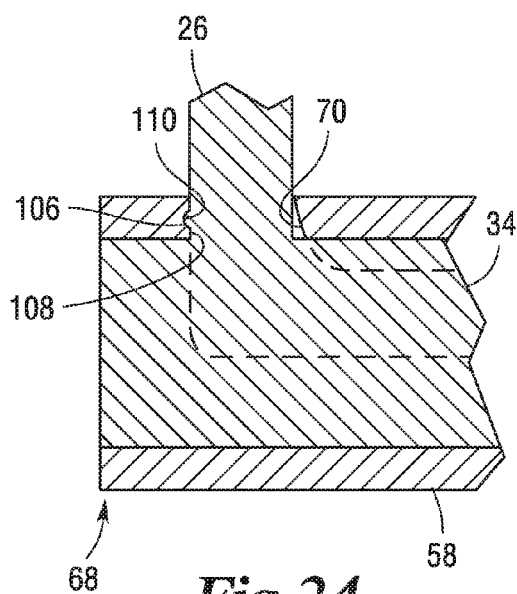
FIG. 24 is a sectioned elevational view taken along lines 24-24 of FIG. 23 of the co-axial actuated scissors of the present invention first shown in FIG. 23.
Figure 25:
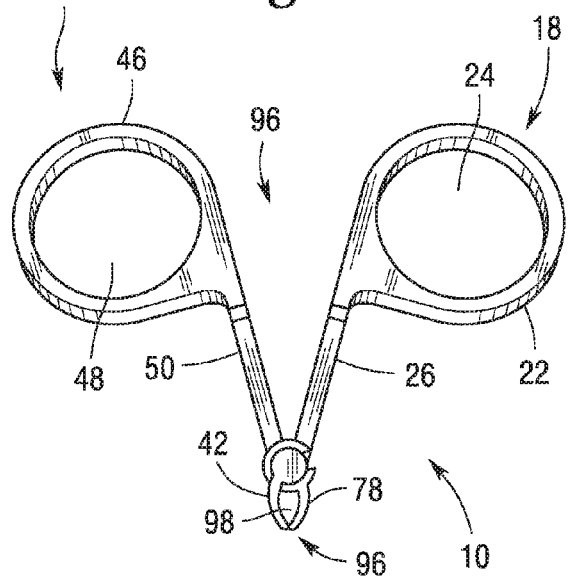
FIG. 25 is a front elevational view of the second alternative preferred embodiment of the co-axial actuated scissors first shown in FIG. 23 illustrating the disposition of the handles and the cutting jaws when the scissors are disposed to the anatomical structure gripping position.
Figure 26:
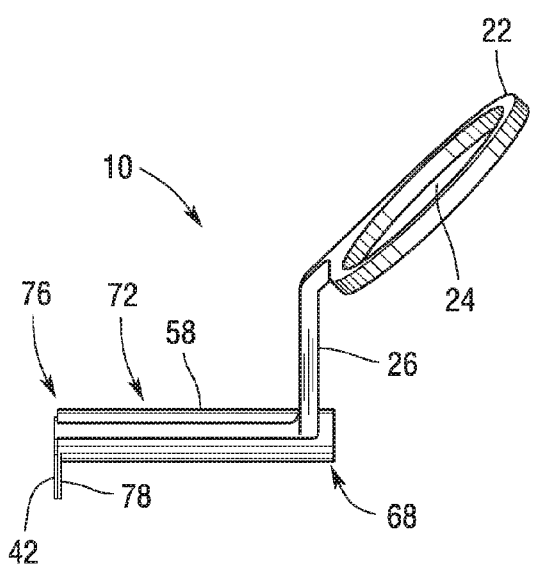
FIG. 26 is a side elevational of the second alternative preferred embodiment of the co-axial actuated scissors of the present invention.

Thus, FIGS. 19 through 22 disclose a first preferred alternative embodiment for scissors 10 wherein a protrusion 102 projects outwardly from the external surface of inner rotating member 34. Protrusion 102 is located at the proximal or handle end 36 of the body of scissors 10. Formed on inner annular surface 62 of primary cylinder 58 are a plurality—three as shown in FIGS. 20 and 21—of spaced-apart generally square-shaped recesses 104 sized to receive and maintain therein protrusion 102 as a function of the movement of handles 22 and 46 to the various surgical detent positions. Thus, recess 104 located at the lowermost position corresponds to fully open position 94, and when protrusion 102 is seated within recess 104 scissors 10 are maintained in fully open position 94 as shown in FIGS. 8a and 15. Recess 104 that is located at the middle position or the nine o'clock position corresponds to anatomical structure gripping position 96 wherein cutting blades 42 and 78 form an aperture 98 for capturing and holding the anatomical structure so that scissors 10 can be properly positioned and oriented prior to cutting the structure. FIG. 20 shows protrusion 102 seated within middle recess 104. Recess 104 located at the uppermost position corresponds to detent fully closed position 100 and when protrusion 102 seats within recess 104 as a result of the closure of handles 22 and 46 and the rotation of inner rotating member 34 relative to primary cylinder 58 cutting jaws 42 and 78 are pivoted toward and past each other for cutting the anatomical structure as shown in FIGS. 8c and 17.

Illustrated in FIGS. 23 through 26 is a second preferred alternative embodiment for the co-axial actuated scissors shown in FIGS. 1 through 18. The alternative embodiment of FIGS. 23 through 26 includes a plurality—at least three—of spaced-apart recesses 106 formed at handle end 68 of second scissor portion 20, and, more specifically, recesses 106 are formed on the portion at handle end 68 of primary cylinder 58 that forms and defines rear face 108 of angulated groove 70. Located at the lowermost position of stem 26 of handle 22 of first scissor portion 18 is a protrusion 110 adapted for successive mating engagement and seating within recesses 106 concomitant with the movement of handles 22 and 46 to various detent positions 94, 96 and 100. The location of each recess 104 on rear face 108 that defines angulated groove 70 corresponds to the three surgical operational positions, i.e., fully open position 94, anatomical structure gripping position 96, and detent fully closed and cutting position 100.

Figure 27:
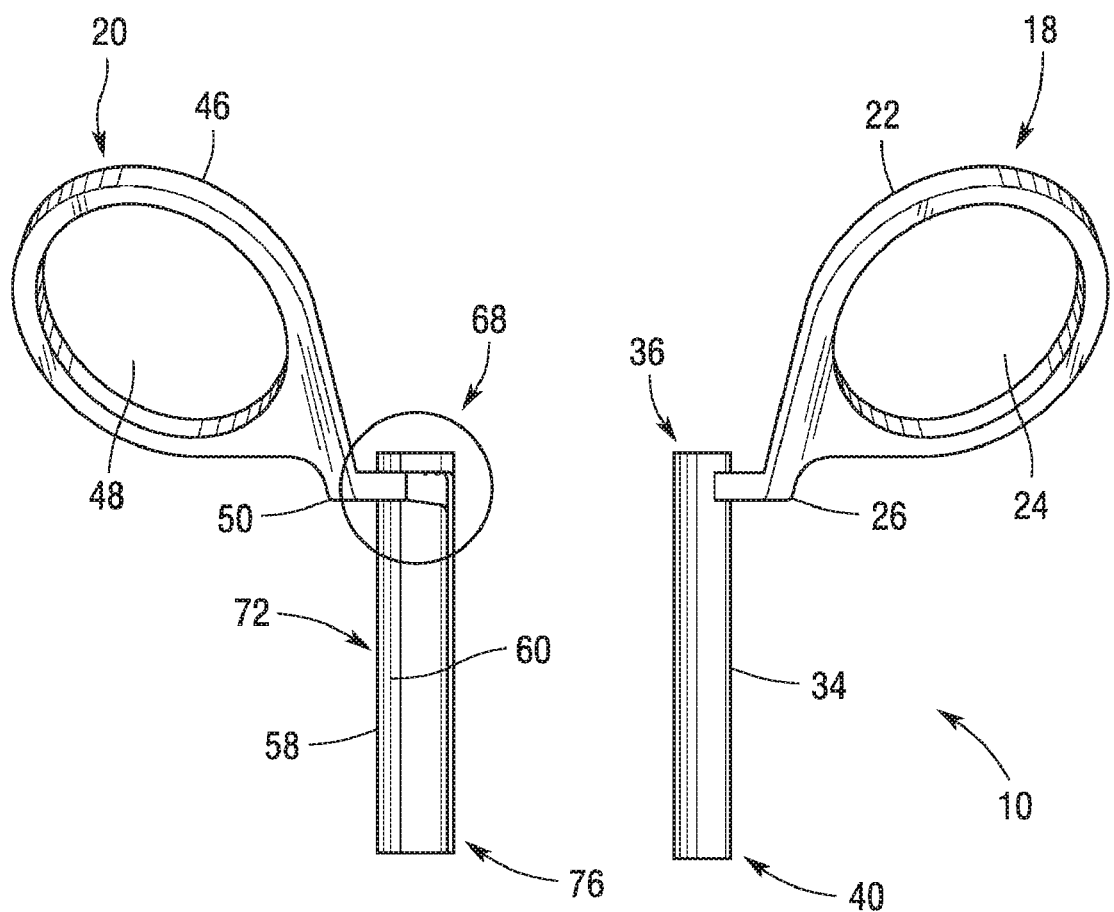
FIG. 27 is a top plan view of third preferred alternative embodiment of the co-axial actuated scissors of the present invention; and, FIG. 28 is an enlarged sectional view of the third preferred alternative embodiment of the co-axial actuated scissors of the present invention first shown in FIG. 27.
Figure 28:
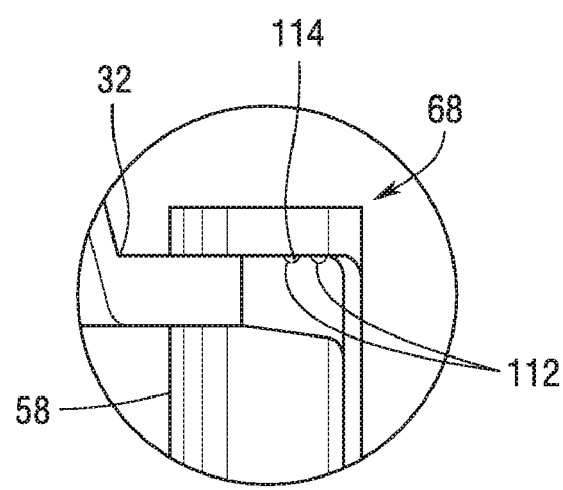

FIGS. 27 and 28 illustrate a third preferred alternative embodiment for scissors 10 first shown in FIGS. 1 through 18. In FIGS. 27 and 28 three spaced-apart recesses 112 are formed at the lower portion of the handle end, and adjacent lower end 32 of stem 26, of first scissor portion 18. The spacing of recesses 112 corresponds, respectively, to fully open position 94, anatomical structure gripping position 96, and fully closed cutting position 100. A protrusion or nubbin 114 on rear face 108 of the slot that the defines angulated groove 70, and which is located at handle end 68 of primary cylinder 58 is adapted for successive seating engagement within recesses 112 concomitant with the opening and closing of handles 22 and 46 and the rotation of inner rotating member 34 and primary cylinder 58.

The above-described preferred and alternative embodiments are intended, by way of example, to illustrate the principles of the invention but not in any way to limit the scope of the claims. Thus, numerous other alterations, variations, and modifications can be made by those skilled in the art without departing from the spirit of the invention or the scope of the appended claims.

I claim:

1. Co-axial actuated scissors for use in a surgical procedure of cutting an immediately adjacent and parallel longitudinal anatomic structure in a plane normal to a main longitudinal axis extending through a working body of said scissors, comprising:

a first scissor portion including an inner elongated rotating member and a first handle attached to said inner elongated rotating member;

a second scissor portion including a distally and laterally open furrow or groove of elongated C-shaped cross-section and a second handle attached adjacent to said distally and laterally open furrow or groove of C-shaped cross-section;

said elongated C-shaped second portion including a distally tally and laterally open furrow or groove for allowing the telescopic slidable assembly of said inner rotating member within said elongated C-shaped second portion so that both said inner rotating member and said elongated C-shaped second portion are able to coaxially rotate relative to each other along their shared and identical main longitudinal axis during use of said scissors in said surgical procedure;

said telescopic assembly of said inner rotating member to said elongated C-shaped second portion creating a working body that includes a proximal end adjacent to the attachment of said first and said second handles to said inner rotating member and said elongated C-shaped second portion and an opposite distal end;

said working body defining said main longitudinal axis that extends through said concentrically assembled inner rotating member and said elongated C-shaped second portion;

said first handle and said second handle being offset from said main longitudinal axis at an angle that is between 0 degrees and 90 degrees;

a pair of cutting jaws located at said distal end of said working body with one cutting jaw mounted to said inner rotating member for rotational movement therewith and the other cutting jaw mounted to said elongated C-shaped member for rotational movement therewith and the cutting action of said cutting jaws occurring normal to said main longitudinal axis;

detent positioning means for determining surgical operational positions of said scissors that includes a fully open position, an anatomical structure non-contact encompassing position and a fully closed position whereby the engagement of said detent positioning means is concurrent with the movements of said first and said second handles, said coaxial rotations of said inner rotating member and said elongated C-shaped member and the movement of said cutting jaws whereupon movement of said first and said second handles to said fully open position allows a surgeon to place said scissors over and in proximity to said anatomical structure, movement of said first and said second handles to said anatomical structure non-contact encompassing position causes said cutting jaws to fully surround but not touch said anatomical structure and while simultaneously allowing said surgeon to otherwise longitudinally and frictionlessly slide and push said scissors in no other device-related dimensionally-restricted fashion along said cross-sectionally encompassed anatomical structure to determine the optimum surgical cutting position; and, closure of said first and said second handles upon each other results in the further coaxial rotation of said inner rotating member and said elongated C-shaped member and concomitant rotation of said cutting jaws for completely severing said anatomical structure.

2. Co-axial actuated scissors for use in a surgical procedure for cutting an elongated anatomical structure in a plane normal to a main longitudinal axis of said scissors and parallel main longitudinal anatomic structure axis, comprising:
  a first elongated member;
  a C-shaped second elongated member, said second elongated member including a void for receiving therein said first elongated member so that said first and said second elongated members can concentrically rotate relative to each other during said surgical procedure;
  assembly of said first elongated member to said second elongated member forming a working body that defines the main longitudinal axis and through which said main longitudinal axis extends;
  said working body including a handle end and an opposite distal end;
  a first handle attached to said first elongated member adjacent said handle end;
  a second handle attached to said second elongated member adjacent said handle end;
  a jaw attached to said first elongated member for rotation therewith and the other cutting jaw attached to said second elongated member for rotation therewith and said cutting jaws extending in a plane that is normal to said main longitudinal axis so that the severing of said anatomical structure occurs normal to said main longitudinal axis;
  said first and said second handles being movable to a fully open position, an anatomical structure non-contact encompassing position and a fully closed cutting position with the movements of said first and said second handles resulting in the concurrent rotation of said first and said second elongated members and said rotation of said cutting jaws;
  detent positioner for maintaining said first and said second handles at said fully open position and said anatomical structure non-contact encompassing position and whereupon movement of said handles to said fully open position causes said cutting jaws to open so that said surgeon can orient and position said scissors over and in proximity to said anatomical structure whereby movement of said handles to said anatomical structure non-contact encompassing position causes said concurrent rotation of said first and said second elongated members and said closure of said cutting jaws about said anatomical structure so that said scissors can fully encompass the entire cross-section of and frictionlessly slide upon said anatomical structure for optimal placement thereon; and
  movement of said first and said second handles to said fully closed position causes the closure of said first and second handles upon each other and further rotations of said first and said second elongated members and said cutting jaws for completely severing said anatomical structure.

3. Co-axial actuated scissors for use in a surgical procedure of cutting an elongated and immediately adjacent and axially parallel anatomical structure in a plane normal to a main longitudinal axis extending through a working body of said scissors, comprising:
  a first scissor portion including an inner elongated rotating member and a first handle attached to said inner elongated rotating member;
  a C-shaped second scissor portion including a elongated furrow or groove and a second handle attached adjacent to said elongated furrow or groove;
  said elongated C-shaped portion including a distally and laterally open void for allowing the telescopic slidable assembly of said inner rotating member within said elongated C-shaped portion so that both said inner rotating member and said elongated C-shaped portion are able to coaxially rotate relative to each other during use of said scissors in said surgical procedure;
  said telescopic assembly of said inner rotating member to said elongated C-shaped portion creating a working body that includes a proximal end adjacent to the attachment of said first and said second handles to said inner rotating member and said elongated C-shaped portion and an opposite distal end;
  said working body defining said main longitudinal axis that extends through said concentrically assembled inner rotating member and said elongated C-shaped portion;
  said first handle and said second handle being offset from said main longitudinal axis at an angle that is between 0 degrees and 90 degrees;
  a pair of symmetric and semicircular or arcuate cutting jaws located at said distal end of said working body with one cutting jaw mounted to said inner rotating member for rotational movement therewith and the other cutting jaw mounted to said elongated C-shaped portion for rotational movement therewith and the cutting action of said cutting jaws occurring normal to said main longitudinal axis;
  a detent positioner having an arcuate arm laterally extending from said second handle and transverse to said main longitudinal axis, said detent positioner determines surgical operational positions of said scissors that includes a fully open position, an anatomical structure non-contact encompassing position and a fully closed position whereby the engagement of said decent positioning means is concurrent with the movements of said first and said second handles, said coaxial rotations of said inner rotating member and said elongated C-shaped portion and the movement of said cutting jaws whereupon movement of said first and said second handles to said fully opal position allows a surgeon to place said scissors over and in proximity to said anatomical structure, movement of said first and said second handles to said anatomical structure non-contact encompassing position causes said cutting jaws to cross-sectionally surround said anatomical structure and allows said surgeon to frictionlessly slide and push said scissors along said anatomical structure to determine the optimum surgical cutting position; and,
  closure of said first and said second handles upon each other results in the further coaxial rotation of said inner rotating member and said primary member and concomitant rotation of said cutting jaws for completely severing said anatomical structure.

4. Co-axial actuated scissors for use in a surgical procedure for cutting an elongated and parallel longitudinal anatomic structure in a plane normal to a main longitudinal axis of said scissors, comprising:
  a first elongated member;
  a C-shaped second elongated member, said second elongated member including a void for receiving therein said first elongated member so that said first and said second elongated members can concentrically rotate relative to each other during said surgical procedure;

assembly of said first elongated member to said second elongated member forming a working body that defines the main longitudinal axis and through which said main longitudinal axis extends;
said working body including a handle end and an opposite distal end;
a first handle attached to said first elongated member adjacent said handle end;
a second handle attached to said second elongated member adjacent said handle end;
a pair of cutting jaws located at said distal end with one cutting jaw attached to said first elongated member for rotation therewith and the other cutting jaw attached to said second elongated member for rotation therewith and said cutting jaws extending in a plane that is normal to said main longitudinal axis so that the severing of said anatomical structure occurs normal to said main longitudinal axis;
said first and said second handles being movable to a fully open position, an anatomical structure non-contact encompassing position and a fully closed cutting position with the movements of said first and said second handles resulting in the concurrent rotation of said first and said second elongated members and said rotation of said cutting jaws;
a detent positioner having an arcuate arm mounted to said second handle and extending transverse to said main longitudinal axis, said detent positioner maintains said first and said second handles at said fully open position and said anatomical structure non-contact encompassing position and whereupon movement of said handles to said fully open position causes said cutting jaws to open so that said surgeon can orient and position said scissors over and in proximity to said anatomical structure whereby movement of said handles to said anatomical structure non-contact encompassing position causes said concurrent rotation of said first and said second elongated members and said distal contact of said cutting jaws completely and circumferentially surrounds said anatomical structure so that said scissors can slide frictionlessly upon said anatomical structure for optimal placement thereon; and
movement of said first and said second handles to said fully closed position causes the closure of said first and second handles upon each other and further rotations of said first and said second elongated members and said cutting jaws for completely severing said anatomical structure.

5. The scissors of claim 3 wherein said detent positioner includes an arcuate arm laterally extending from said second handle and transverse to said main longitudinal axis.

6. The scissors of claim 5 wherein said detent positioner includes a receiving notch formed on said first handle and which is sized to accommodate the passage therethrough of said arm.

7. The scissors of claim 6 wherein said arm includes a first detent and a second detect for discretely engaging said receiving notch concurrent with the movement of said handles during said surgical procedure.

8. The scissors of claim 7 wherein the engagement of said first detent with said receiving notch corresponds to said fully open position of said scissors for orienting and positioning said scissors in proximity to said anatomical structure to be cut.

9. The scissors of claim 8 wherein the engagement of said second detent with said receiving notch corresponds to said anatomical structure non-contact encompassing position whereupon said cutting jaws contact one another only at their most distal tips thus creating an aperture in which to surround and otherwise cross-sectionally retain and/or orient said scissors relative to said anatomical structure so that said scissors can be frictionlessly moved or slid along said anatomical structure in order to determine the optimal surgical cutting position.

10. The scissors of claim 4 wherein said detest positioner means includes an arcuate arm mounted to said second handle and extending transverse to said main longitudinal axis.

11. The scissors of claim 10 wherein said arm includes a first detent and a second detent spaced from said first detent.

12. The scissors of claim 11 wherein said detent positioner includes a receiving notch formed on said first handle of said first elongated member with said receiving notch sized to accommodate the passage therethrough of said arm and the engagement of said first detent and said second detent.

13. The scissors of claim 12 wherein the engagement of said first detent with said receiving notch corresponds to said fully open position and the engagement of said second detent with said receiving notch corresponds to said anatomical structure non-contact encompassing position.

* * * * *